US010117611B2

(12) United States Patent
Kobayashi et al.

(10) Patent No.: US 10,117,611 B2
(45) Date of Patent: Nov. 6, 2018

(54) BIOLOGICAL SIGNAL MEASURING SYSTEM AND BIOLOGICAL SIGNAL MEASURING APPARATUS

(71) Applicant: NIHON KOHDEN CORPORATION, Tokyo (JP)

(72) Inventors: Naoki Kobayashi, Tokyo (JP); Hideaki Hirabara, Tokyo (JP); Shinya Nagata, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 101 days.

(21) Appl. No.: 14/161,195

(22) Filed: Jan. 22, 2014

(65) Prior Publication Data

US 2014/0213865 A1    Jul. 31, 2014

(30) Foreign Application Priority Data

Jan. 31, 2013    (JP) ................................. 2013-017230

(51) Int. Cl.
*A61B 5/1455*    (2006.01)
*A61B 5/00*    (2006.01)

(52) U.S. Cl.
CPC ........ *A61B 5/14552* (2013.01); *A61B 5/0053* (2013.01); *A61B 5/6826* (2013.01)

(58) Field of Classification Search
CPC .............. A61B 5/14552; A61B 5/1491; A61B 5/14551; A61B 5/02416; A61B 5/1459;
(Continued)

(56) References Cited

U.S. PATENT DOCUMENTS 4,776,339 A * 10/1988 Schreiber ........... A61B 5/14552
   600/324
4,854,699 A *  8/1989 Edgar, Jr. ........... A61B 5/14551
   356/41

(Continued)

FOREIGN PATENT DOCUMENTS

CN    1315844 A    10/2001
CN    1985764 A    6/2007
(Continued)

OTHER PUBLICATIONS

Extended European Search Report for the related European Patent Application No. 14152094.0 dated Sep. 4, 2014.
(Continued)

*Primary Examiner* — Eric Winakur
*Assistant Examiner* — Chu Chuan (JJ) Liu
(74) *Attorney, Agent, or Firm* — Kenealy Vaidya LLP

(57) ABSTRACT

A biological signal measuring system includes: a light emitter emitting a first light beam and a second light beam; a light receiver outputting first and second signals in accordance with light intensities of the first and second light beams that have been passed through or reflected from a living tissue of a subject; a first calculating section acquiring a light attenuation of the first light beam based on the first signal and a light attenuation of the second light beam based on the second signal; a second calculating section acquiring a blood-derived light attenuation based on the light attenuation of the first and second light beams; a third calculating section acquiring information relating to a blood oxygen saturation based on a change amount of the blood-derived light attenuation associated with pressurization of the living tissue; and an outputting section outputting the acquired information.

20 Claims, 7 Drawing Sheets

(58) Field of Classification Search
CPC ....... A61B 5/0059; A61B 5/1455; A61B 5/68; A61B 5/6801; A61B 5/6813; A61B 5/72; A61B 5/0205; A61B 5/6826
See application file for complete search history.

(56) References Cited

U.S. PATENT DOCUMENTS

| | | | |
|---|---|---|---|
| 5,119,815 A * | 6/1992 | Chance | G01J 3/2889 356/341 |
| 5,459,700 A * | 10/1995 | Jacobs | A61M 25/1018 368/10 |
| 5,782,756 A * | 7/1998 | Mannheimer | A61B 5/14542 600/322 |
| 5,827,181 A * | 10/1998 | Dias | A61B 5/0055 600/322 |
| 6,213,952 B1 | 4/2001 | Finarov et al. | |
| 6,400,972 B1 | 6/2002 | Fine | |
| 6,587,704 B1 | 7/2003 | Fine et al. | |
| 6,594,513 B1 | 7/2003 | Jobsis et al. | |
| 6,711,424 B1 * | 3/2004 | Fine | A61B 5/1455 600/322 |
| 6,801,798 B2 * | 10/2004 | Geddes | A61B 5/14552 600/323 |
| 6,931,268 B1 | 8/2005 | Kiani-Azarbayjany et al. | |
| 2004/0024297 A1 | 2/2004 | Chen et al. | |
| 2007/0043281 A1 * | 2/2007 | Fine | A61B 5/0048 600/335 |
| 2007/0149872 A1 | 6/2007 | Zhang et al. | |
| 2011/0046464 A1 | 2/2011 | Debreczeny et al. | |
| 2012/0130211 A1 | 5/2012 | Kobayashi et al. | |
| 2014/0114152 A1 * | 4/2014 | Fournier | A61B 5/14552 600/324 |

FOREIGN PATENT DOCUMENTS

| | | | |
|---|---|---|---|
| CN | 102525444 A | 7/2012 | |
| CN | 102579053 A | 7/2012 | |
| CN | 102715893 A | 10/2012 | |
| JP | 2-305555 A | 12/1990 | |
| JP | 5-503856 A | 6/1993 | |
| JP | 2006-75354 A | 3/2006 | |
| WO | 91/11137 A1 | 8/1991 | |
| WO | 03/039326 A2 | 5/2003 | |
| WO | 2012/087634 A2 | 6/2012 | |

OTHER PUBLICATIONS

Partial European Search Report for the related European Patent Application No. 14152094.0 dated May 23, 2014.
Japanese Office Action for the related Japanese Patent Application No. 2013-017230 dated Jun. 7, 2016.
Chinese Office Action for the related Chinese Patent Application No. 201410032632.6 dated Nov. 3, 2017.

* cited by examiner

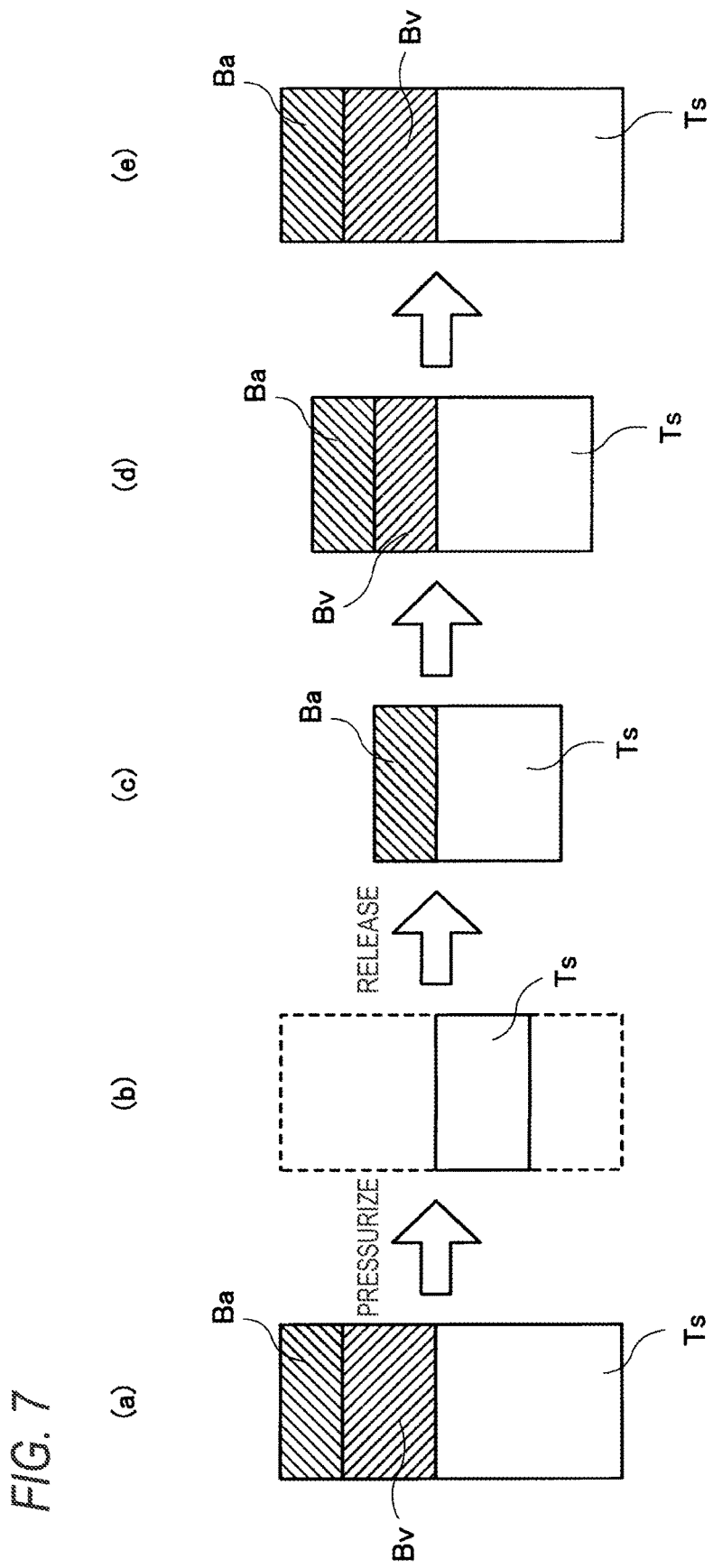

BIOLOGICAL SIGNAL MEASURING SYSTEM AND BIOLOGICAL SIGNAL MEASURING APPARATUS

CROSS-REFERENCE TO RELATED APPLICATION(S)

This application is based upon and claims the benefit of priority from prior Japanese patent application No. 2013-017230, filed on Jan. 31, 2013, the entire contents of which are incorporated herein by reference.

BACKGROUND

The presently disclosed subject matter relates to a biological signal measuring system, and more particularly to a system for identifying the blood oxygen saturation based on a biological signal acquired from a subject that is an example of the living body. The presently disclosed subject matter relates also to a biological signal measuring apparatus which is to be used in the system.

Measurement of the degree of oxygenation of blood is important for determining whether blood is sufficiently supplied to the living tissue or not. The degree of oxygenation of arterial blood, i.e., the arterial oxygen saturation can be easily measured by using a pulse oximeter. In measurement of the degree of oxygenation of whole blood including venous blood, i.e., the blood oxygen saturation, however, a NIRS (Near InfraRed Spectroscopy) sensor is usually used (for example, see U.S. Pat. No. 6,213,952).

In the case of measurement by using a NIRS sensor, optical path lengths for a plurality of near infrared light beams passed through the living tissue are varied depending on the wavelength, and a measurement result contains influences due to light attenuations caused by tissue (skin and the like) other than blood (hereinafter, such tissue is referred to as non-blood tissue). Although qualitative knowing about the blood oxygen saturation can be obtained, therefore, it is impossible to obtain a quantitative measurement value.

SUMMARY

The presently disclosed subject matter may provide a technique in which information relating to the blood oxygen saturation can be acquired by a simple method.

There may be provided a biological signal measuring system comprising: a light emitter which is configured to emit a first light beam having a first wavelength, and a second light beam having a second wavelength; a light receiver which is configured to output first and second signals respectively in accordance with received light intensities of the first and second light beams that have been passed through or reflected from a living tissue of a subject; a first calculating section which is configured to acquire a light attenuation of the first light beam based on the first signal, and a light attenuation of the second light beam based on the second signal; a second calculating section which is configured to acquire a blood-derived light attenuation based on the light attenuation of the first light beam, and the light attenuation of the second light beam; a third calculating section which is configured to acquire information relating to a blood oxygen saturation, based on an amount of change of the blood-derived light attenuation associated with pressurization of the living tissue; and an outputting section which is configured to output the acquired information.

The third calculating section may identify a level of the blood oxygen saturation with respect to a reference value, based on an increase or decrease of the change of the blood-derived light attenuation.

When the amount of the change of the blood-derived light attenuation is larger than a predetermined value, the acquisition of the information by the third calculating section may be automatically started.

The biological signal measuring system may further comprise: a cuff which is adapted to be attachable to the subject so as to pressurize the living tissue; and a cuff pressure controlling section which is configured to control an air pressure inside the cuff.

There may be provided a biological signal measuring apparatus comprising: a signal receiving section which is configured to receive a first signal corresponding to an intensity of a first light beam that has been passed through or reflected from a living tissue of a subject, and that has a first wavelength, and a second signal corresponding to an intensity of a second light beam that has been passed through or reflected from the living tissue, and that has a second wavelength; a first calculating section which is configured to acquire a light attenuation of the first light beam based on the first signal, and a light attenuation of the second light beam based on the second signal; a second calculating section which is configured to acquire a blood-derived light attenuation based on the light attenuation of the first light beam, and the light attenuation of the second light beam; a third calculating section which is configured to acquire information relating to a blood oxygen saturation, based on an amount of change of the blood-derived light attenuation associated with pressurization of the living tissue; and an outputting section which is configured to output the acquired information.

There may be provided a method of controlling a biological signal measuring apparatus comprising a signal receiving section which is configured to receive a first signal corresponding to an intensity of a first light beam that has been passed through or reflected from a living tissue of a subject, and that has a first wavelength, and a second signal corresponding to an intensity of a second light beam that has been passed through or reflected from the living tissue, and that has a second wavelength, the method comprising: acquiring a light attenuation of the first light beam based on the first signal, and a light attenuation of the second light beam based on the second signal; acquiring a blood-derived light attenuation based on the light attenuation of the first light beam, and the light attenuation of the second light beam; acquiring information relating to a blood oxygen saturation, based on an amount of change of the blood-derived light attenuation associated with pressurization of the living tissue; and outputting the acquired information.

There may be provided a program causing a computer to execute the method.

There may be provided a non-transitory computer-readable recording medium storing a program causing a computer to execute the method.

There may be provided a biological signal measuring system comprising: a light emitter which is configured to emit a first light beam having a first wavelength, a second light beam having a second wavelength, and a third light beam having a third wavelength; a light receiver which is configured to output first, second, and third signals respectively in accordance with received light intensities of the first, second, and third light beams that have been passed through or reflected from a living tissue of a subject; a first calculating section which is configured to acquire a light attenuation of the first light beam based on the first signal, a light attenuation of the second light beam based on the second signal, and a light attenuation of the third light beam based on the third signal; a second calculating section which is configured to acquire a blood-derived first light attenuation based on a difference of two light attenuations of a first combination which is selected from the light attenuation of the first light beam, the light attenuation of the second light beam, and the light attenuation of the third light beam, and a blood-derived second light attenuation based on a difference of two light attenuations of a second combination which is selected from the light attenuation of the first light beam, the light attenuation of the second light beam, and the light attenuation of the third light beam; a third calculating section which is configured to identify a blood oxygen saturation based on the blood-derived first light attenuation and the blood-derived second light attenuation; and an outputting section which is configured to output the identified blood oxygen saturation.

The biological signal measuring system may further comprise a monitoring section which is configured to cause the third calculating section to periodically identify the blood oxygen saturation.

The biological signal measuring system may further comprise: a first cuff which is adapted to be attachable to the subject so as to pressurize an upstream side of the living tissue in a blood flow; and a cuff pressure controlling section which is configured to control an air pressure inside the first cuff.

The monitoring section may notify of a timing of pressurizing the living tissue, through the outputting section.

The biological signal measuring system may further comprise a second cuff which is adapted to be attached to the subject in a manner that the second cuff can pressurize the living tissue, and the cuff pressure controlling section may control an air pressure inside the second cuff at a predetermined timing.

There may be provided a biological signal measuring apparatus comprising: a signal receiving section which is configured to receive a first signal corresponding to an intensity of a first light beam that has been passed through or reflected from a living tissue of a subject, and that has a first wavelength, a second signal corresponding to an intensity of a second light beam that has been passed through or reflected from the living tissue, and that has a second wavelength, and a third signal corresponding to an intensity of a third light beam that has been passed through or reflected from the living tissue, and that has a third wavelength; a first calculating section which is configured to acquire a light attenuation of the first light beam based on the first signal, a light attenuation of the second light beam based on the second signal, and a light attenuation of the third light beam based on the third signal; a second calculating section which is configured to acquire a blood-derived first light attenuation based on a difference of two light attenuations of a first combination which is selected from the light attenuation of the first light beam, the light attenuation of the second light beam, and the light attenuation of the third light beam, and a blood-derived second light attenuation based on a difference of two light attenuations of a second combination which is selected from the light attenuation of the first light beam, the light attenuation of the second light beam, and the light attenuation of the third light beam; a third calculating section which is configured to identify a blood oxygen saturation based on the blood-derived first light attenuation and the blood-derived second light attenuation; and an outputting section which is configured to output the identified blood oxygen saturation.

There may be provided a method of controlling a biological signal measuring apparatus comprising a signal receiving section which receives a first signal corresponding to an intensity of a first light beam that has been passed through or reflected from a living tissue of a subject, and that has a first wavelength, a second signal corresponding to an intensity of a second light beam that has been passed through or reflected from the living tissue, and that has a second wavelength, and a third signal corresponding to an intensity of a third light beam that has been passed through or reflected from the living tissue, and that has a third wavelength, the method comprising: acquiring a light attenuation of the first light beam based on the first signal, a light attenuation of the second light beam based on the second signal, and a light attenuation of the third light beam based on the third signal; acquiring a blood-derived first light attenuation based on a difference of two light attenuations of a first combination which is selected from the light attenuation of the first light beam, the light attenuation of the second light beam, and the light attenuation of the third light beam, and a blood-derived second light attenuation based on a difference of two light attenuations of a second combination which is selected from the light attenuation of the first light beam, the light attenuation of the second light beam, and the light attenuation of the third light beam; identifying a blood oxygen saturation based on the blood-derived first light attenuation and the blood-derived second light attenuation; and outputting the identified blood oxygen saturation.

There may be provided a program causing a computer to execute the method.

There may be provided a non-transitory computer-readable recording medium storing a program causing a computer to execute the method.

BRIEF DESCRIPTION OF THE DRAWINGS

FIG. 7 is a diagram illustrating identification of the blood oxygen saturation associated with pressurization of the living tissue.

DETAILED DESCRIPTION OF EXEMPLARY EMBODIMENTS

Figure 1:
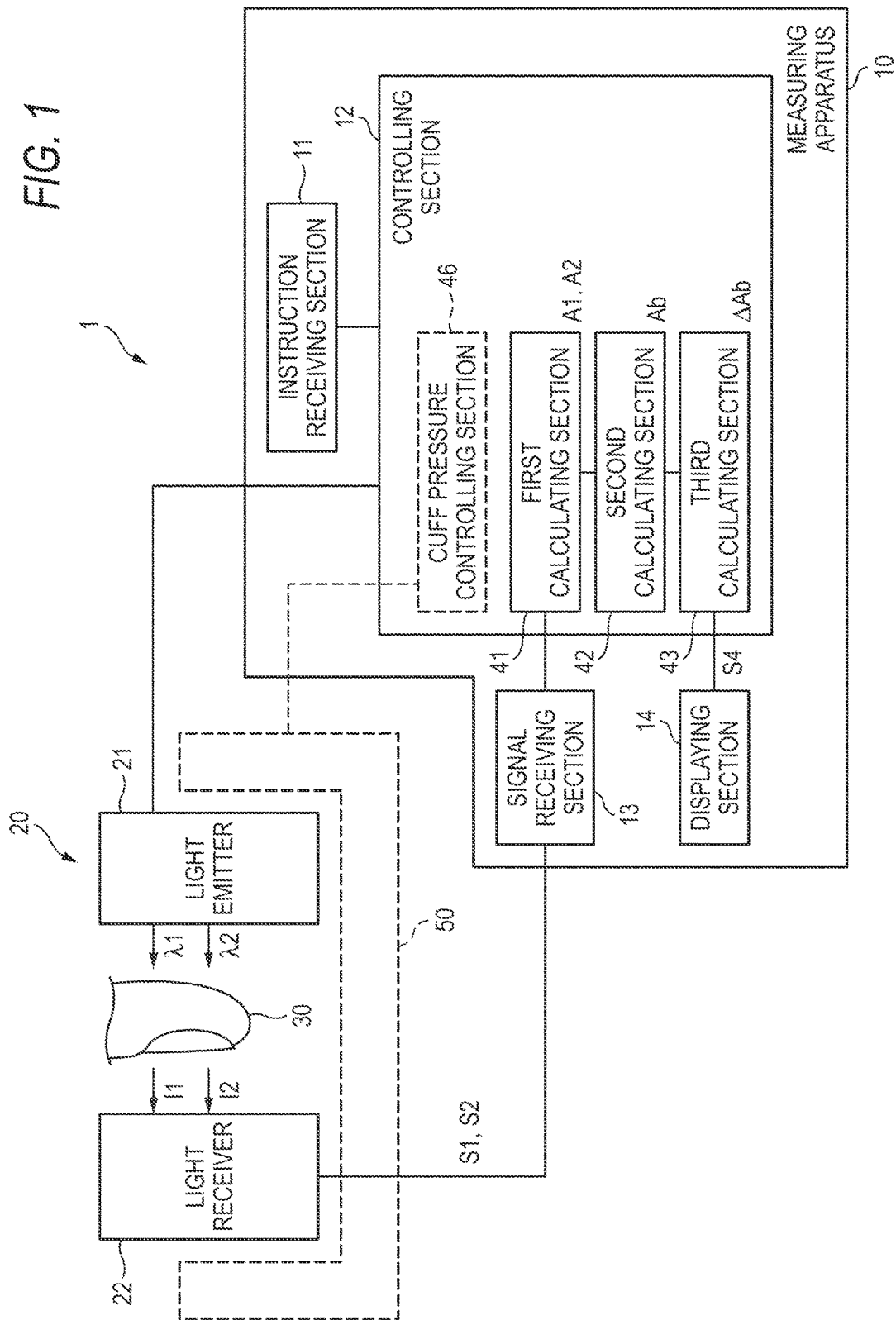
FIG. 1 is a functional block diagram showing the configuration of a biological signal measuring system of a first embodiment of the presently disclosed subject matter.

Embodiments of the presently disclosed subject matter will be described in detail with reference to the accompanying drawings. In the drawings which will be used in the following description, the scale is adequately changed in order to draw components in a recognizable size.

As shown in FIG. 1, a biological signal measuring system 1 of a first embodiment of the presently disclosed subject matter includes a measuring apparatus 10 and a probe 20. The measuring apparatus 10 includes an instruction receiving section 11, a controlling section 12, a signal receiving section 13, and a displaying section 14. The probe 20 has a related-art two-wavelength type configuration which is to be attached to the finger 30 of the subject, and includes a light emitter 21 and a light receiver 22.

The instruction receiving section 11 is a related-art man-machine interface which is disposed on the outer surface of the measuring apparatus 10, and configured so as to be able to receive instructions which are input by the user in order to cause the measuring apparatus 10 to perform a desired operation.

The controlling section 12 includes: a CPU which performs various calculation processes; a ROM which stores various control programs; a RAM which is used as a working area for storing data and executing the programs; and the like, and performs various controls in the measuring apparatus 10. The controlling section 12 is communicably connected to the instruction receiving section 11. The instruction receiving section 11 supplies a signal corresponding to the received instructions, to the controlling section 12.

The light emitter 21 of the probe 20 is communicably connected to the controlling section 12 of the measuring apparatus 10. The light emitter 21 can emit a first light beam having a first wavelength $\lambda 1$, and a second light beam having a second wavelength $\lambda 2$. In the embodiment, the light emitter 21 includes a light emitting diode which emits a red light beam of 660 nm that is an example of the first wavelength $\lambda 1$, and another light emitting diode which emits an infrared light beam of 940 nm that is an example of the second wavelength $\lambda 2$. In accordance with a control signal supplied from the controlling section 12, each of the light emitting diodes emits the light beam at predetermined timings. The emitted first and second light beams enter the finger 30 which is an example of the living tissue.

The light receiver 22 of the probe 20 is placed at a position where the first and second light beams which have been passed through the finger 30 can be received. The light receiver 22 is configured so as to be able to output a first signal S1 corresponding to the intensity I1 of the received first light beam, and a second signal S2 corresponding to the intensity I2 of the received second light beam. In the embodiment, photodiodes are used as devices having such a configuration. The light receiver 22 is communicably connected to the signal receiving section 13 of the measuring apparatus 10. The signals S1, S2 which are output from the light receiver 22 are supplied to the signal receiving section 13.

The signal receiving section 13 is communicably connected to the controlling section 12. The signal receiving section 13 supplies the received signals S1, S2 to the controlling section 12. The controlling section 12 includes a first calculating section 41, a second calculating section 42, and a third calculating section 43.

The first calculating section 41 is configured so as to acquire the light attenuation A1 of the first light beam based on the first signal S1, and the light attenuation A2 of the second light beam based on the second signal S2. Each of the light attenuations A1, A2 is calculated as a ratio of the amount of light of the first or second signal S1 or S2 received at a certain time (for example, during pressurization of the living tissue) to that at another time (for example, before pressurization of the living tissue), and indicated by either of the following expressions:

$$A1 = \log(I1/Io1) \tag{1}$$

$$A2 = \log(I2/Io2) \tag{2}$$

where Io1 and Io2 indicate the amounts of received light at the reference time (for example, before pressurization of the living tissue), and I1 and I2 indicate the amounts of received light at the measurement. The suffix "1" indicates the first light beam, and the suffix "2" indicates the second light beam.

The second calculating section 42 is configured so as to acquire the blood-derived light attenuation based on the light attenuations A1, A2 of the first and second light beams acquired by the first calculating section 41. Specifically, the section is configured so as to acquire the blood-derived light attenuation Ab based on the difference of the light attenuation A1 and the light attenuation A2. The principle of the process will be described in detail below.

A change A in light attenuation which is produced when the finger 30 is pressed to change the thickness of the living tissue is caused by a change in thickness of blood and that of thickness of the non-blood tissue. This fact is indicated by the following expressions:

$$A1 = Ab1 + 1 = E1HbDb + Z1Dt \tag{3}$$

$$A2 = Ab2 + At2 = E2HbDb + Z2Dt \tag{4}$$

where E indicates the absorption coefficient (dl $g^{-1}cm^{-1}$), Hb indicates the hemoglobin concentration (g $dl^{-1}$), Z indicates the light attenuation factor ($cm^{-1}$) of the non-blood tissue, and D indicates the changed thickness (cm). The suffix "b" indicates blood, the suffix "t" indicates the non-blood tissue, the suffix "1" indicates the first light beam, and the suffix "2" indicates the second light beam.

The wavelength dependency of the non-blood tissue can be neglected. Therefore, it can be deemed that Z1=Z2. When Expression (3) is subtracted from Expression (4), the following is obtained:

$$A2 - A1 = (E2 - E1)HbDb \tag{5}$$

The right side contains only information of blood. When the difference of the light attenuation A1 and the light attenuation A2 is obtained, therefore, it is possible to acquire the blood-derived light attenuation Ab.

Figure 2:
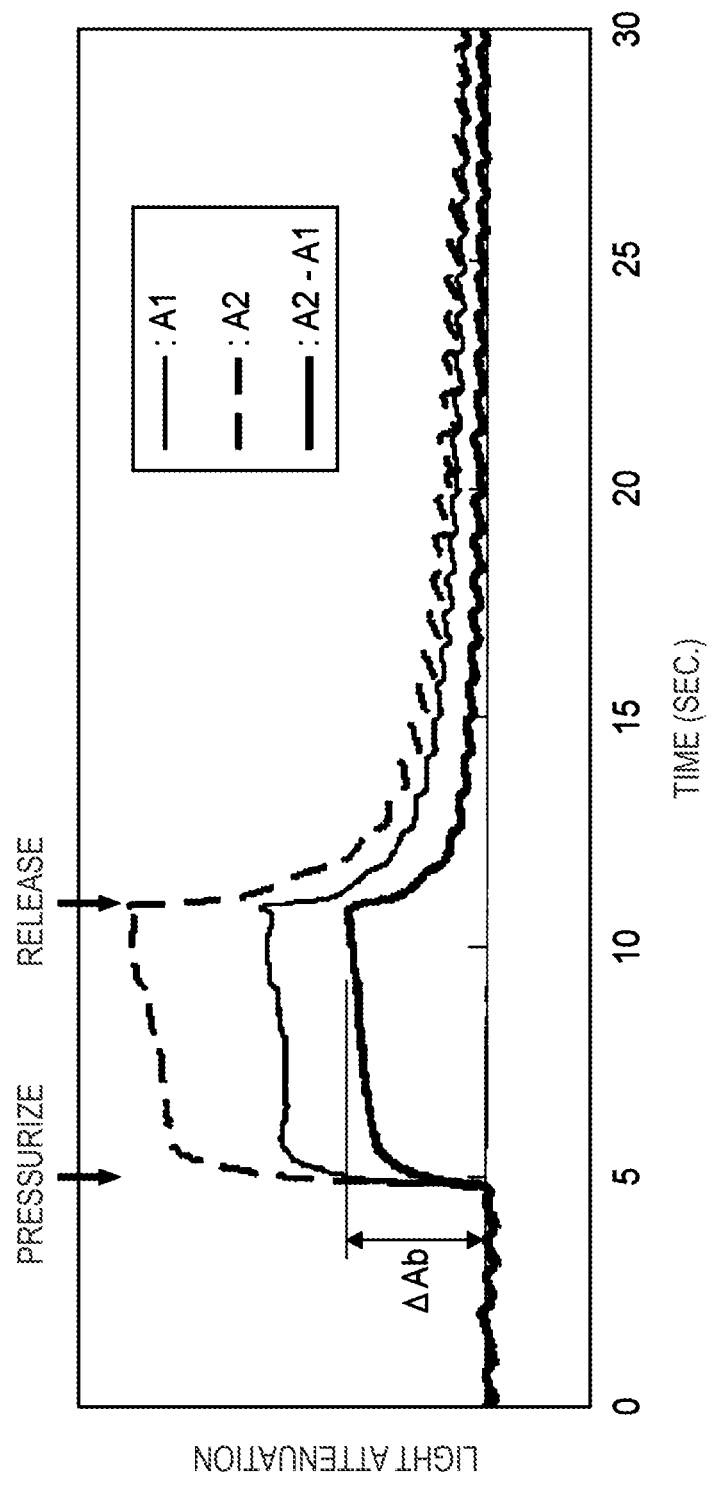
FIG. 2 is a view illustrating an example of a process which is performed by a second calculating section of the biological signal measuring system.

FIG. 2 shows a graph showing temporal changes of the light attenuation A1, the light attenuation A2, and the blood-derived light attenuation Ab (=A2−A1) in the case where the finger 30 is pressed through the probe 20.

It is seen that, even when the pressurization is released, the values of the light attenuations A1, A2 do not return to the levels which are attained before the start of the pressurization, and the deformation of the non-blood tissue exerts influence. It is also seen that, after the release of the pressurization, the difference (A2−A1) of the light attenuations, i.e., the blood-derived light attenuation Ab converges to the level which is attained before the start of the pressurization. Namely, the influence caused by the deformation of the non-blood tissue can be eliminated by a simple calculation process in which the difference of the light attenuations that are obtained by irradiating the tissue with light beams of different wavelengths is calculated.

Here, (E2−E1) in Expression (5) is a function of the blood oxygen saturation. The absorption coefficients E1, E2 are indicated by the following expressions, respectively:

$$E1 = Eo1 S + Er1(1-S) \quad (6)$$

$$E2 = Eo2 S + Er2(1-S) \quad (7)$$

where Eo indicates the absorption coefficient of oxyhemoglobin, Er indicates the absorption coefficient of reduced hemoglobin, and S indicates the blood oxygen saturation. Similarly with the above, the suffix "1" indicates the first light beam, and the suffix "2" indicates the second light beam.

Figure 3A:
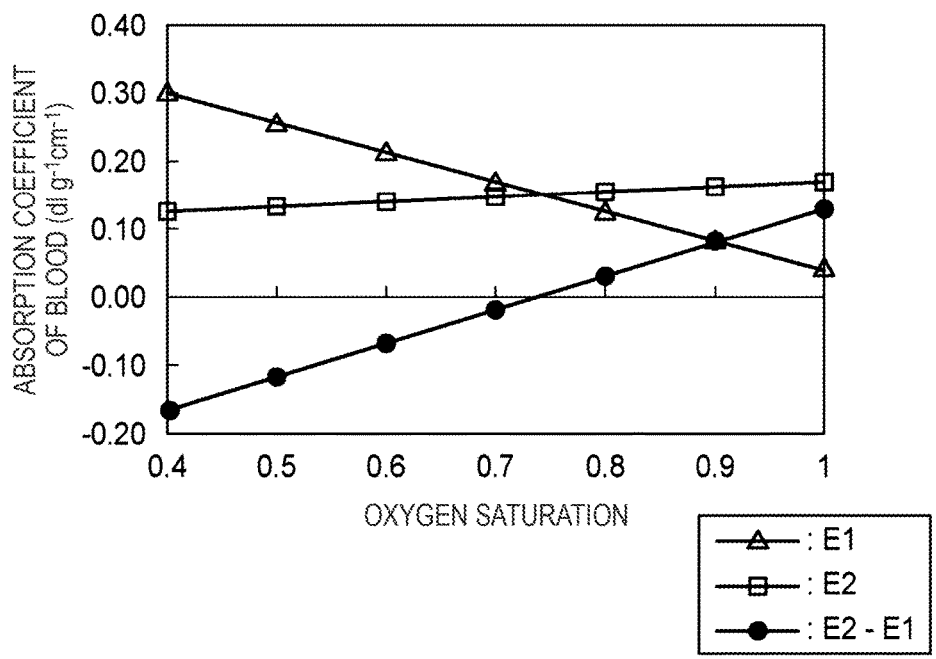
FIGS. 3A and 3B are views illustrating relationships between the change amount of the light attenuation and the blood oxygen saturation.
Figure 3B:
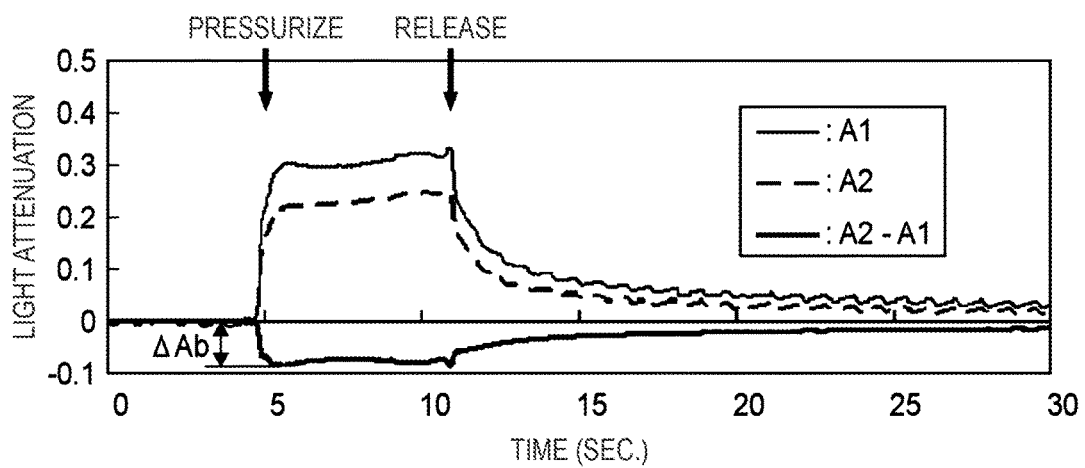

FIG. 3A shows relationships between the absorption coefficients E1, E2, and (E2−E1), and the blood oxygen saturation S. The sign of the value of (E2−E1) is reversed at the blood oxygen saturation S=0.74. Similarly with FIG. 2, FIG. 3A shows a graph showing temporal changes of the light attenuation A1, the light attenuation A2, and the blood-derived light attenuation Ab (=A2−A1) in the case where the finger 30 is pressed through the probe 20. FIG. 3A shows the case where the value of (E2−E1) is negative.

From the above, it is seen that, when the change amount of the blood-derived light attenuation Ab associated with pressurization of the finger 30 is observed, information of the blood oxygen saturation S can be acquired. When the blood-derived light attenuation Ab is changed in the reducing direction, namely, it is possible to determine that the blood oxygen saturation S is smaller than 0.74. In the blood oxygen saturation S, the value of 0.74 is very smaller than the normal value. The situation where the blood oxygen saturation is smaller than this value means that the condition of the subject requires emergency medical care. Also in the case where the blood-derived light attenuation Ab is changed in the increasing direction, a small change amount means that the blood oxygen saturation S is in the vicinity of 0.74, and therefore it is recognizable that the condition of the subject is not normal.

In the embodiment, therefore, the third calculating section 43 is configured so as to acquire information relating to the level of the blood oxygen saturation S based on the change amount ΔAb of the blood-derived light attenuation Ab (=A2−A1) which is acquired by the second calculating section 42, and which is associated with pressurization of the finger 30.

Specifically, the third calculating section 43 is configured so as to acquire the differential value of the blood-derived light attenuation Ab which is acquired by the second calculating section 42. When the light attenuation Ab is rapidly raised because of pressurization of the living tissue, the differential value is largely changed. When blood is evacuated from the place to which pressurization is applied, the light attenuation Ab has a substantially constant value in the vicinity of the maximum value, and therefore the differential value drifts around zero. The third calculating section 43 is configured so as to recognize that the living tissue is pressed, through a large change of the initial differential value, and acquire the change amount ΔAb at a timing when the differential value then begins to drift in the vicinity of zero.

Based on the acquired change amount ΔAb, then, the third calculating section 43 determines whether the blood oxygen saturation is higher or lower than the reference value (in the embodiment, 0.74) of the blood oxygen saturation S. When the change amount ΔAb is negative, or when the change of the blood-derived light attenuation Ab associated with pressurization of the finger 30 is in the reducing direction, it is determined that the blood oxygen saturation S is smaller than the reference value (the condition of the subject is in an abnormal state in which the severity is relatively high). When the change amount ΔAb is positive, or when the change of the blood-derived light attenuation Ab associated with pressurization of the finger 30 is in the increasing direction, it is determined that the blood oxygen saturation S is larger than the reference value.

The displaying section 14 which is an example of the outputting section is a related-art display device which is disposed on the outer surface of the measuring apparatus 10. The displaying section 14 is communicably connected to the controlling section 12. The controlling section 12 supplies a signal S4 indicative of a result of the determination which is performed by the third calculating section 43, to the displaying section 14. The displaying section 14 displays the determination result in an adequate manner corresponding to the signal S4.

According to the configuration of the embodiment, the absolute value of the blood oxygen saturation S cannot be acquired. When performing a simple work of attaching the existing probe 20 which is to be used in pulse oximetry, to the finger 30 of the subject, and pressing the finger 30 through the probe 20, however, a medical person can obtain a certain result of determination about the level of the blood oxygen saturation S. In a scene of triage, for example, information relating to the blood oxygen saturation S can be provided simply and rapidly without requiring preparation of a special probe and performing a special work. This can contribute to rapid determination of the priority.

In the case where the change amount ΔAb has a positive value, the determination result can be further divided. In the case where the change amount ΔAb has a positive value and the absolute value is small, the value is considered to be near S=0.74 or the reference value, and it is determined that the condition of the subject is in an abnormal state in which the severity is relatively low. In the case where the absolute value of the change amount ΔAb is large to some extent, it is determined that the condition of the subject is in a normal state. When such a determination result is supplied to the displaying section 14, more detail information of the blood oxygen saturation S can be provided.

The foregoing description of the first embodiment has been made in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

The light receiver 22 is not always required to be placed at a position where the light beams which have been passed through the finger 30 can be received. Alternatively, a configuration may be employed where the light receiver is placed at a position where light beams which have been reflected from the finger 30 are received, and the light attenuations are acquired based on the reflection intensities of light beams of different wavelengths.

The living tissue to which the probe 20 is to be attached is not limited to the finger 30. Any kind of living tissue may be selected as the object as far as the desired measurement can be performed. For example, the earlobe may be used as the object.

Figure 4A:
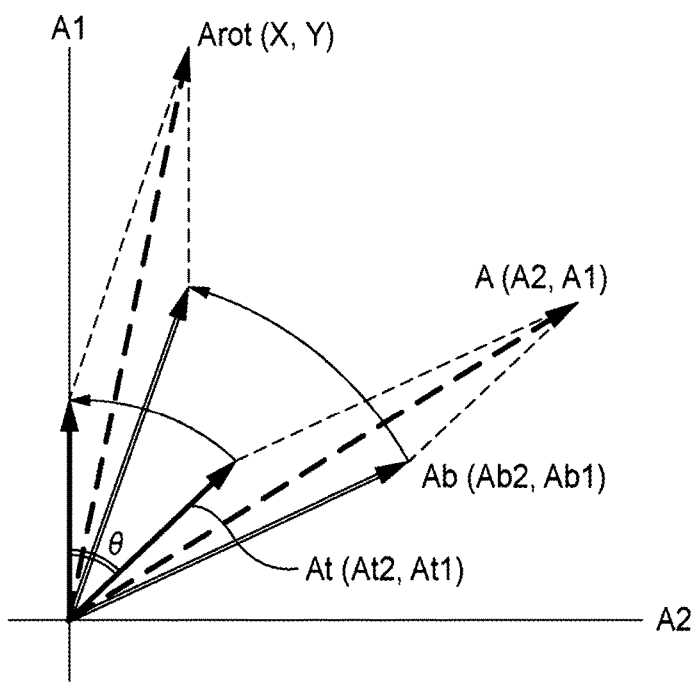
FIGS. 4A and 4B are views illustrating another example of the process which is performed by the second calculating section.
Figure 4B:
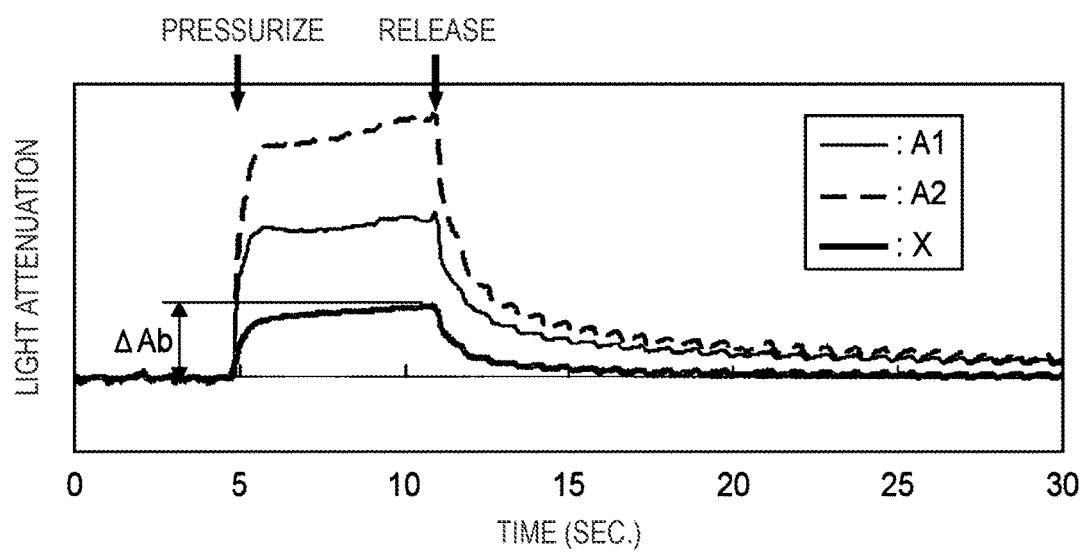

The process in which the second calculating section 42 acquires the blood-derived light attenuation is not always required to be performed based on the difference of the light attenuation A1 and the light attenuation A2. FIGS. 4A and 4B are views illustrating another example of the process which is performed by the second calculating section 42, and in which the rotation matrix is used.

In FIG. 4A, the Y-axis indicates the light attenuation A1 of the first light beam, the X-axis indicates the light attenuation A2 of the second light beam, and the light attenuation A at a certain time is expressed by a vector having components (A2, A1). The vector A is given in the form of a resultant vector of a vector having components (Ab2, Ab1) and indicating the blood-derived light attenuation Ab, and a vector having components (At2, At1) and indicating the light attenuation At derived from the non-blood tissue.

When the vector A is rotated by θ in a coordinate space, a vector Arot is obtained. It is seen that the component derived from the non-blood tissue is eliminated from the X-axis component of the vector Arot, and the vector Arot consists of only the blood-derived component. This operation is expressed by the following expression:

$$\text{Arot}^T = KA^T \quad (8)$$

In the above expression, K and A are expressed by the following matrixes, respectively.

$$K = \begin{pmatrix} \cos\theta & -\sin\theta \\ \sin\theta & \cos\theta \end{pmatrix} \quad (9)$$

$$A = (A2 \quad A1)$$

The light attenuation At derived from the non-blood tissue does not depend on the wavelength. In FIG. 4A, therefore, At1=At2. Consequently, $\theta = (\pi/2) = -\tan^{-1}$ (At1/At2) is attained.

FIG. 4B shows the temporal change of the value of the X-coordinate of the thus obtained vector Arot together with the temporal changes of the light attenuations A1, A2. It is seen that, even when the pressurization is released, the values of the light attenuations A1, A2 do not return to the levels which are attained before the start of the pressurization, and the light attenuations are affected by deformation of the non-blood tissue. By contrast, it is seen that, after the release of the pressurization, the value of the X-coordinate of Arot, i.e., the blood-derived light attenuation Ab converges to the level which is attained before the start of the pressurization. Namely, the influence caused by deformation of the non-blood tissue can be eliminated by applying a simple rotation calculation to a matrix acquired from the values of light attenuations which are obtained by irradiating the tissue with light beams of different wavelengths.

A configuration may be employed where the process of acquiring information relating to the blood oxygen saturation S in the third calculating section 43 is performed when the instruction receiving section 11 receives instructions for starting measurement. Another configuration may be employed where the process is automatically started when the change amount of the blood-derived light attenuation Ab acquired by the second calculating section 42 exceeds a predetermined value. The determination on whether the change amount of the blood-derived light attenuation Ab exceeds the predetermined value or not may be conducted based on the fact that the light attenuation Ab acquired by the second calculating section 42 exceeds a predetermined threshold, or the fact that the differential value Ad acquired by the third calculating section 43 exceeds a predetermined threshold.

Usually, such a large change is not produced in the light attenuation Ab as far as usual measurement by pulse oximetry is performed. When a large change occurs in the light attenuation Ab, therefore, it is possible to determine that the possibility that the living tissue has been pressed in order to identify the blood fill time is high. In a configuration where the blood fill time is automatically identified based on the determination, the burden on the operator can be further reduced.

As an effect of the presently disclosed subject matter, the unnecessity of preparation of a special probe in the case where information relating to the blood oxygen saturation S is to be acquired has been described. This is not intended to inhibit the use of additional equipment. A configuration may be employed where, as indicated by the broken lines in FIG. 1, a cuff 50 which covers the probe 20 is attached to the finger 30 of the subject, and the controlling section 12 further includes a cuff pressure controlling section 46 which controls the air pressure inside the cuff 50.

The cuff pressure controlling section 46 first pressurizes the interior of the cuff 50 so that the finger 30 of the subject can be pressed at a predetermined pressure through the probe 20. After elapse of a predetermined time period, the interior of the cuff 50 is depressurized. According to the configuration, the pressurization can be always performed under constant conditions irrespective of the operator or the repeat number. Therefore, information relating to the blood oxygen saturation S can be acquired more correctly.

The functions of the first to fifth calculating sections 41 to 45 and cuff pressure controlling section 46 which are described above can be realized by the operation of hardware such as circuit devices, that of software such as programs stored in the computer-readable recording medium or the controlling section 12 which is an example of the computer, or a combination of these operations.

Next, a biological signal measuring system 1A of a second embodiment of the presently disclosed subject matter will be described in detail with reference to FIG. 5. The components which are identical or similar to those of the biological signal measuring system 1 of the first embodiment are denoted by the same reference numerals, and duplicated description will be omitted.

The biological signal measuring system 1A of the embodiment includes a measuring apparatus 10A and a probe 20A. The measuring apparatus 10A includes the instruction receiving section 11, a controlling section 12A, the signal receiving section 13, and the displaying section 14. The probe 20A in the embodiment has a related-art three-wavelength type configuration which is to be attached to the finger 30 of the subject, and includes a light emitter 21A and a light receiver 22A.

The light emitter 21A of the probe 20A is communicably connected to the controlling section 12A of the measuring apparatus 10A. The light emitter 21A can emit the first light beam having the first wavelength λ1, the second light beam having the second wavelength λ2, and a third light beam having a third wavelength λ3. In the embodiment, the light emitter 21A includes the light emitting diode which emits the red light beam of 660 nm that is an example of the first wavelength λ1, the light emitting diode which emits the infrared light beam of 940 nm that is an example of the second wavelength λ2, and another light emitting diode which emits an infrared light beam of 810 nm that is an example of the third wavelength λ3. In accordance with a control signal supplied from the controlling section 12A, each of the light emitting diodes emits the light beam at predetermined timings. The emitted first, second, and third light beams enter the finger 30 which is an example of the living tissue.

The light receiver 22A of the probe 20A is placed at a position where the first, second, and third light beams which have been passed through the finger 30 can be received. The light receiver 22A is configured so as to be able to output the first signal S1 corresponding to the intensity I1 of the received first light beam, the second signal S2 corresponding to the intensity I2 of the received second light beam, and a third signal S3 corresponding to the intensity I3 of the received third light beam. In the embodiment, photodiodes are used as devices having such a configuration. The light receiver 22A is communicably connected to the signal receiving section 13 of the measuring apparatus 10A. The signals S1, S2, S3 which are output from the light receiver 22A are supplied to the signal receiving section 13.

The signal receiving section 13 is communicably connected to the controlling section 12A. The signal receiving section 13 supplies the received signals S1, S2, S3 to the controlling section 12A. The controlling section 12A includes a first calculating section 41A, a second calculating section 42A, a third calculating section 43A, and a monitoring section 44.

The first calculating section 41A is configured so as to acquire the light attenuation A1 of the first light beam based on the first signal S1, the light attenuation A2 of the second light beam based on the second signal S2, and the light attenuation A3 of the third light beam based on the third signal S3. Each of the light attenuations A1, A2, A3 is calculated as a ratio of the amount of light of the first, second, or third signal S1, S2, or S3 received at a certain time (for example, during pressurization of the living tissue) to that at another time (for example, before pressurization of the living tissue), and indicated by either of the following expressions:

$$A1 = \log(I1/Io1) \tag{10}$$

$$A2 = \log(I2/Io2) \tag{11}$$

$$A3 = \log(I3/Io3) \tag{12}$$

where Io1, Io2, and Io3 indicate the amount of received light at the reference time (for example, before pressurization of the living tissue), and I1, I2, and I3 indicate the amount of received light at the measurement. The suffix "1" indicates the first light beam, the suffix "2" indicates the second light beam, and the suffix "3" indicates the third light beam.

The second calculating section 42A is configured so as to acquire the blood-derived light attenuation based on the light attenuations A1, A2 of the first and second light beams acquired by the first calculating section 41A, and the light attenuations A2, A3 of the second and third light beams. Specifically, the section is configured so as to acquire a blood-derived light attenuation Ab21 (an example of the first light attenuation) based on the difference of the light attenuation A1 and the light attenuation A2, and acquire a blood-derived light attenuation Ab23 (an example of the second light attenuation) based on the difference of the light attenuation A2 and the light attenuation A3. The principle of the process will be described in detail below.

A change A in light attenuation which is produced when the finger 30 is pressed to change the thickness of the living tissue is caused by a change in thickness of blood and that of thickness of the non-blood tissue. This fact is indicated by the following expressions:

$$A1 = Ab1 + At1 = E1HbDb + Z1Dt \tag{13}$$

$$A2 = Ab2 + At2 = E2HbDb + Z2Dt \tag{14}$$

$$A3 = Ab3 + At3 = E3HbDb + Z3Dt \tag{15}$$

where E indicates the absorption coefficient (dl g$^{-1}$cm$^{-1}$), Hb indicates the hemoglobin concentration (g dl$^{-1}$), Z indicates the light attenuation factor (cm$^{-1}$) of the non-blood tissue, and D indicates the thickness (cm). The suffix "b" indicates blood, the suffix "t" indicates the non-blood tissue, the suffix "1" indicates the first light beam, the suffix "2" indicates the second light beam, and the suffix "3" indicates the third light beam.

The wavelength dependency of the non-blood tissue can be neglected. Therefore, it can be deemed that Z1=Z2=Z3. When Expression (13) is subtracted from Expression (14), and Expression (15) is subtracted from Expression (14), the followings are obtained:

$$Ab21 = A2 - A1 = (E2 - E1)HbDb \tag{16}$$

$$Ab23 = A2 - A3 = (E2 - E3)HbDb \tag{17}$$

The right sides contain only information of blood. When the difference of the light attenuation A1 and the light attenuation A2, and that of the light attenuation A2 and the light attenuation A3 are obtained, therefore, it is possible to acquire the blood-derived light attenuations Ab21, Ab23. Next, Expression (16) is divided by Expression (17), the terms of Hb and Db are deleted, and the following expression is obtained:

$$Ab21/Ab23 = (A2-A1)/(A2-A3) = (E2-E1)/(E2-E3) \tag{18}$$

In Expression (18), (E2−E1) and (E2−E3) are functions of the blood oxygen saturation S. The absorption coefficients E1, E2, E3 are expressed by the following expressions, respectively:

$$E1 = Eo1S + Er1(1-S) \tag{19}$$

$$E2 = Eo2S + Er2(1-S) \tag{20}$$

$$E3 = Eo3S + Er3(1-S) \tag{21}$$

where Eo indicates the absorption coefficient of oxyhemoglobin, Er indicates the absorption coefficient of reduced hemoglobin, and S indicates the blood oxygen saturation. Similarly with the above, the suffix "1" indicates the first light beam, the suffix "2" indicates the second light beam, and the suffix "3" indicates the third light beam.

Figure 6A:
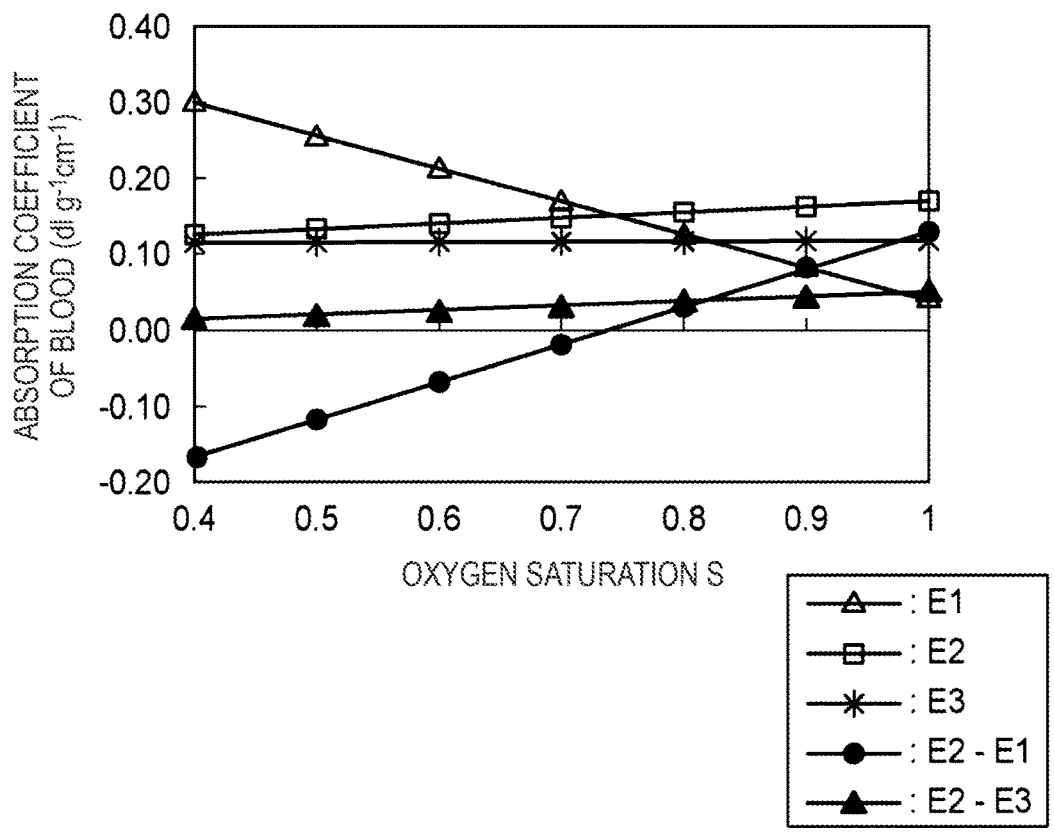
FIGS. 6A and 6B are views illustrating relationships between the absorption coefficient and the blood oxygen saturation.
Figure 6B:
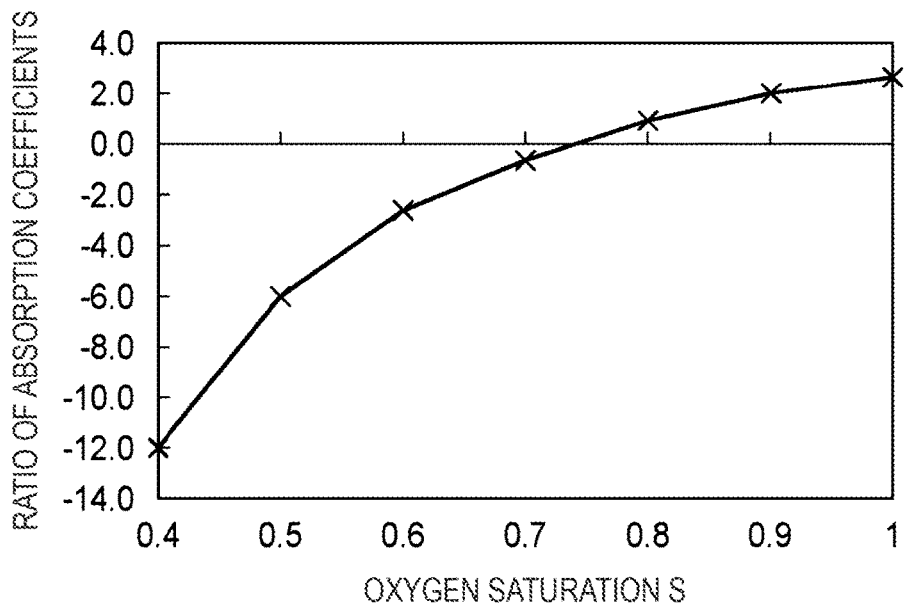

FIG. 6A shows relationships between the absorption coefficients E1, E2, E3, and (E2−E1) and (E2−E3), and the blood oxygen saturation S. As shown in FIG. 6B, therefore, also the ratio of (E2−E1) and (E2−E3) is a function of the blood oxygen saturation S.

From the above, it is seen that, when the blood-derived light attenuations Ab21, Ab23 are measured by using at least three light beams having different wavelengths, the blood oxygen saturation S can be quantitatively identified through Expressions (18) to (21). The third calculating section 43A is configured so as to identify the blood oxygen saturation S based on the principle.

The controlling section 12A supplies a signal S4 indicative of a result of the determination which is performed by the third calculating section 43A, to the displaying section 14. The displaying section 14 displays the determination result in an adequate manner corresponding to the signal S4.

According to the configuration of the embodiment, the blood oxygen saturation S can be identified only by attaching the probe 20A for pulse oximetry in which measurement is conducted by using three or more wavelengths, to the finger 30 of the subject. In a scene of triage, for example, the blood oxygen saturation S can be identified simply and rapidly by using a multi-wavelength pulse oximeter and without requiring preparation of a special probe and performing a special work. This can contribute to rapid determination of the priority.

The monitoring section 44 is configured so as to perform a monitoring process. In the monitoring process, the third calculating section 43A is caused to periodically perform the operation of identifying the blood oxygen saturation S. Specifically, when it is recognized that the finger 30 is pressed, the process is started, and, each elapse of a predetermined time period, the third calculating section 43A is caused to identify the blood oxygen saturation S.

According to the configuration, the condition of the peripheral circulation of the subject can be continuously monitored. This assists to know the condition of the patient during surgery or in an intensive care unit. This will be described with reference to FIG. 7.

As shown in (a) of FIG. 7, the finger 30 to which the prove 20A is attached includes arterial blood Ba, venous blood Bv, and non-blood tissue Ts. When the finger 30 in this state is pressed, as shown in (b) of FIG. 7, the tissue Ts is compressed, and arterial blood Ba and venous blood Bb are eliminated. When the pressing is released, as shown in (c) of FIG. 7, arterial blood Ba first starts to flow in, and the thickness of the tissue Ts begins to return to the original value. As shown in (d) of FIG. 7, then, venous blood Bb starts to flow in. In FIG. 7, (e) shows a situation where the thicknesses of arterial blood Ba, venous blood Bb, and the tissue Ts return to the states which are attained before the start of the pressurization.

After the pressing is released, as the thickness of the finger 30 returns to the original value, the light attenuation becomes larger. The change of the light attenuation contains components respectively contributed by thickness changes of arterial blood Ba, venous blood Bv, and the tissue Ts. In the above-described technique, the blood oxygen saturation S can be identified while eliminating the influence caused by the change of the tissue Ts. At the timing shown in (c) of FIG. 7, the blood oxygen saturation S has a value which is substantially equal to the arterial oxygen saturation. As venous blood Bv flows in as shown in (d) and (e) of FIG. 7, the component contributed by venous blood Bv becoming larger in the light attenuation, and the blood oxygen saturation S is lowered to a fixed value. When the value and the time period which elapses before the saturation reaches the value are checked through the displaying section 14, it is possible to know the condition of the peripheral circulation of the subject.

According to the configuration of the embodiment, the value of the blood oxygen saturation S at an arbitrary timing can be identified. For example, the amounts of received light which are measured at the timing shown in (a) of FIG. 7 are set as the reference values (Io1, Io2, and Io3 in Expressions (10) to (12)), and those of received light which are measured at the timing shown in (b) are deemed to have I1, I2, and I3 in the expressions. Then, it is possible to measure the oxygen saturation of the blood which is eliminated by the pressurization. The change in light attenuation which is calculated from measurements value that, while setting the amounts of received light measured at the timing shown in (b) of FIG. 7 as the reference values, are acquired at a subsequent arbitrary timing can be deemed to be substantially caused by a change in thickness of blood. Therefore, more accurate monitoring of the blood oxygen saturation S can be continuously performed.

In the determination that the finger 30 is pressed, the same technique as that which has been described with reference to the third calculating section 43 in the first embodiment may be used. Namely, the monitoring section 44 is configured so as to acquire the differential value of the blood-derived light attenuation which is acquired by the second calculating section 42A. When the initial large change of the differential value is detected, it is recognized that the tissue is pressed, and, at a timing when the differential value then begins to drift in the vicinity of zero, it is determined that blood is eliminated. This is used as a trigger for starting the measurement.

When performing a simple work of attaching the probe 20A for pulse oximetry in which measurement is conducted by using three or more wavelengths, to the finger 30 of the subject, and pressing the finger 30 through the probe 20A, therefore, a medical person can measure the blood oxygen saturation S of the fingertip at the timing of pressing, and moreover can monitor the subsequent temporal change. When the monitoring is performed while comparing the blood oxygen saturation with the arterial oxygen saturation (SpO2) which can be similarly acquired by the probe 20A, it is possible to know a change in condition of the peripheral circulation of, for example, the patient who is during surgery or in an intensive care unit.

The foregoing description of the second embodiment has been made in order to facilitate understanding of the presently disclosed subject matter, and is not intended to limit the presently disclosed subject matter. It is a matter of course that the presently disclosed subject matter may be changed or improved without departing the spirit thereof, and includes equivalents thereof.

The light receiver 22A is not always required to be placed at a position where the light beams which have been passed through the finger 30 can be received. Alternatively, a configuration may be employed where the light receiver is placed at a position where light beams which have been reflected from the finger 30 are received, and the light attenuations are acquired based on the reflection intensities of light beams of different wavelengths.

The living tissue to which the probe 20A is to be attached is not limited to the finger 30. Any kind of living tissue may be selected as the object as far as the desired measurement can be performed. For example, the earlobe may be used as the object.

The process in which the second calculating section 42A acquires the blood-derived light attenuations Ab21, Ab23 is not always required to be performed based on the differences of the light attenuation A1 and the light attenuation A2, and the light attenuation A2 and the light attenuation A3. As described with respect to the second calculating section 42 in the first embodiment with reference to FIGS. 4A and 4B, the blood-derived light attenuations Ab21, Ab23 may be acquired by using the rotation matrix.

The combinations of the light attenuations which are used in the process of acquiring the blood-derived light attenuations are not limited to the combination of the light attenuations A1, A2, and that of the light attenuations A2, A3. Arbitrary ones of light attenuations may be selected as far as two of combinations of the three kinds of the light attenuations A1, A2, A3 are selected. For example, a combination of the light attenuations A1, A2, and that of the light attenuations A1, A3 may be selected. Alternatively, light beams having four or more wavelengths may be used, and different combinations of acquired four or more kinds of light attenuations may be selected.

As one of disease conditions of diabetes, a phenomenon in that the oxygen partial pressure of the living tissue is reduced is known. The reduction of the oxygen partial pressure is caused by a reduction of the blood oxygen saturation. A comparison of the blood oxygen saturation S which is measured by pressing the living tissue, with that obtained from a healthy person can provide a certain guideline for determining whether diabetes occurs or not. In septicemia, a shunt blood flow is increased, oxygen is not sufficiently supplied to a capillary vessel, and the blood oxygen saturation is lowered. Therefore, a measurement of the blood oxygen saturation is effective also in knowing a clinical condition of the patient with septicemia.

In a measurement which is performed on the tip of a finger of the hand or foot, when the height of the fingertip of the hand or foot is changed, it is possible to change the perfusion pressure and blood volume of the tissue under measurement. Information relating to the tissue blood volume and metabolism can be obtained by measuring a change in blood oxygen saturation which occurs in this case.

When stimulation of temperature, pain, sound, electricity, vision, or the like is applied to the living body, the neural activity causes the heart rate, the peripheral vascular resistance, etc. to be changed, and also the blood oxygen saturation to be changed. In the case where the responsiveness is checked in combination with such stimulation, the system can be used in diagnosis of a disease which causes the nervous system to be changed, such as diabetes, an index of anesthetic depth, and the like.

As one of effects of the presently disclosed subject matter, the unnecessity of preparation of a special probe in the case where the blood oxygen saturation S is to be identified has been described. This is not intended to inhibit the use of additional equipment. A configuration may be employed where, as indicated by the broken lines in FIG. 5, a cuff 51 (an example of the first cuff) is attached upstream of the fingertip (the pressed living tissue), and the controlling section 12A further includes a cuff pressure controlling section 46A which controls the air pressure inside the cuff 51.

The cuff pressure controlling section 46A increases the air pressure of the interior of the cuff 51 so that the blood flow to the finger 30 can be cut off. When the blood oxygen saturation S is continuously measured in this state, the system can be applied to diagnosis of a disease in which a disorder occurs in the metabolism, such as diabetes or septicemia.

As one of disease conditions of diabetes, a phenomenon in that oxygen metabolism is not sufficiently performed in the living tissue is known. In the case where the blood flow to the living tissue is cut off as described above, oxygen is consumed by this tissue, with the result that the blood oxygen saturation S is reduced. In the case where oxygen metabolism is not sufficiently performed, however, the reduction degree of the blood oxygen saturation S is small. When the blood oxygen saturation S is continuously monitored, and the reduction degree is compared with that of a healthy person, therefore, it is possible to provide a certain guideline for determining whether diabetes occurs or not. In septicemia, a shunt blood flow is increased, oxygen is not sufficiently supplied to a capillary vessel, and the blood oxygen saturation is lowered. Therefore, a measurement of the blood oxygen saturation is effective also in knowing the clinical condition of the patient with septicemia.

The internal pressure of the cuff 51 is not always required to be controlled by the cuff pressure controlling section 46A of the measuring apparatus 10A. The pressure may be manually adjusted as far as the blood flow to the finger 30 can be cut off.

As described above, the reference value of the amounts of received light is obtained by means of pressurization of the finger 30, thereby enabling a subsequent measurement of the blood oxygen saturation S to be continuously performed. When the positional relationships of the probe 20A and the living tissue are lost during the measurement, however, the measurement cannot be correctly performed unless the reference value is updated. Therefore, the measurement by means of pressurization is periodically performed, and the reference value is continued to be updated, whereby the reliability of the measurement can be improved. Consequently, the monitoring section 44 may be configured so as to, each elapse of a predetermined time period, notify of the timing of pressurization through the displaying section 14. When a medical person presses the finger 30 in accordance with the notification, it is possible to surely perform periodic identification of the blood oxygen saturation S.

Figure 5:
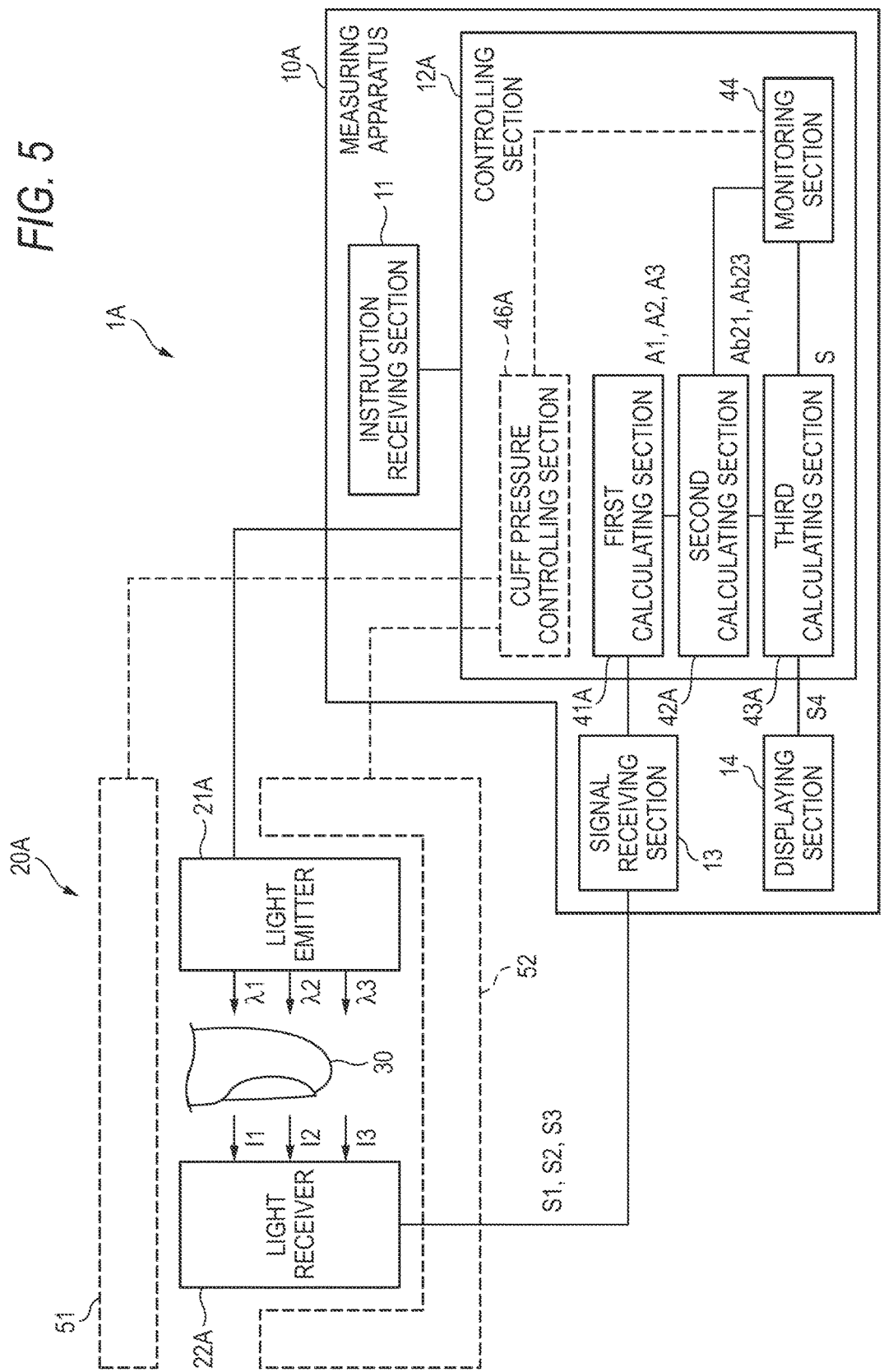
FIG. 5 is a functional block diagram showing the configuration of a biological signal measuring system of a second embodiment of the presently disclosed subject matter.

Alternatively, a configuration may be employed where, as indicated by the broken lines in FIG. 5, a cuff 52 (an example of the second cuff) which cover the probe 20A is attached to the finger 30 of the subject, and the cuff pressure controlling section 46A controls the air pressure inside the cuff 52 at a predetermined timing. For example, the predetermined timing is a timing when the monitoring section 44 causes the third calculating section 43A to identify the blood oxygen saturation S. The internal pressure of the cuff 52 is periodically raised to pressurize the finger 30, so that periodic identification of the blood oxygen saturation S can be automated.

The identified blood oxygen saturation S is not always required to be displayed on the displaying section 14 in the form of numerals. In addition to or in place of this, a color or symbol indicative of the blood oxygen saturation S may be displayed on the displaying section 14, or a sound indicative of the blood oxygen saturation S may be output.

The functions of the first to third calculating sections 41A, 42A, 43A, monitoring section 44, and cuff pressure controlling section 46A which are described above can be realized by the operation of hardware such as circuit devices, that of software such as programs stored in the computer-readable recording medium or the controlling section 12A which is an example of the computer, or a combination of these operations.

According to as aspect of the presently disclosed subject matter, by using the fact that the change amount of the blood-derived light attenuation associated with pressurization of the living tissue is a function of the blood oxygen saturation, a certain result of determination about the level of the blood oxygen saturation can be obtained although it is impossible to identify the absolute value of the blood oxygen saturation. In order to obtain the determination result, the operator is requested only to perform a substantial work of attaching an existing probe which is to be used in, for example, pulse oximetry, to the living issue of the subject and pressing the probe. Namely, it is not required to prepare a special probe and perform a special work. In a scene of triage, for example, this can contribute to rapid determination of the priority.

According to an aspect of the presently disclosed subject matter, when the change amount of the blood-derived light attenuation is larger than a predetermined value, the acquisition of the information may be automatically started. In the case where a large change is made in the blood-derived light attenuation, it is possible to determine that the probability that the living tissue is pressed is high. When information relating to the blood oxygen saturation is automatically acquired base on the determination, the burden on the operator can be further reduced.

According to as aspect of the presently disclosed subject matter, the cuff attachable to the subject so as to pressurize the living tissue, and the cuff pressure controlling section which is configured to control an air pressure inside the cuff may further provided. In this case, the pressurization can be always performed under constant conditions irrespective of the operator or the repeat number. Therefore, information relating to the blood oxygen saturation can be acquired more correctly.

According to as aspect of the presently disclosed subject matter, when two kinds of blood-derived light attenuations are acquired by using the three kinds of wavelengths, only relationships between the absorption coefficient and the blood oxygen saturation can be extracted, and the absolute value of the blood oxygen saturation can be identified. In order to obtain the determination result, the operator is requested only to perform a substantial work of attaching an existing probe for pulse oximetry in which measurement is conducted by using, for example, three or more wavelengths, to the living issue of the subject. Although it is not required to prepare a special probe and perform a special work, the blood oxygen saturation can be rapidly identified by using a multi-wavelength pulse oximeter.

According to as aspect of the presently disclosed subject matter, the blood oxygen saturation may be periodically identified. In this case, the condition of the peripheral circulation of the subject can be continuously monitored. This assists to know the condition of the patient during surgery or in an intensive care unit.

According to as aspect of the presently disclosed subject matter, the first cuff attachable to the subject so as to pressurize an upstream side of the living tissue in a blood flow, and the cuff pressure controlling section which is configured to control an air pressure inside the first cuff may be provided. In this case, when a temporal change of the blood oxygen saturation is observed in a state where the blood flow to the living tissue is cut off, it is possible to obtain an index of the oxygen consumption rate of the living tissue. This can be applied to diagnosis of disease in which a disorder occurs in tissue metabolism, such as diabetes or septicemia.

In order to correctly identify the blood oxygen saturation, it is desirable to press the living tissue each time. According to an aspect of the presently disclosed subject matter, a timing of pressurizing the living tissue may be notified through the outputting section. In this case, the operator is required only to perform pressurization based on the notification, and therefore periodic identification of the blood oxygen saturation can be surely performed.

Alternatively, the second cuff which is to be attached to the subject in a manner that the second cuff can pressurize the living tissue, and the cuff pressure controlling section configured so that the internal air pressure of the second cuff is controlled at a predetermined timing may be provided. In this case, periodic identification of the blood oxygen saturation can be automated.

What is claimed is:

1. A biological signal measuring system comprising:
   a light emitter which is configured to emit a first light beam having a first wavelength, and a second light beam having a second wavelength;
   a light receiver which is configured to output first and second signals respectively in accordance with received light intensities of the first and second light beams that have been passed through or reflected from a living tissue of a subject, wherein the living tissue includes neither arterial blood nor venous blood at a first state and includes at least one of arterial blood and venous blood at a second state;
   a controller configured to:
   (i) acquire a first light attenuation of the first light beam based on the first signal at the first state and the first signal at the second state, and a second light attenuation of the second light beam based on the second signal at the first state and the second signal at the second state;
   (ii) acquire a blood-derived light attenuation based on the first light attenuation and the second light attenuation; and
   (iii) acquire information relating to a blood oxygen saturation, based on an amount of change of the blood-derived light attenuation; and
   an outputting device which is configured to output the acquired information,
   wherein the controller is configured to identify a level of the blood oxygen saturation with respect to a reference value, based on an increase or decrease of the change of the blood-derived light attenuation measured during a time period between the first state and the second state.

2. The biological signal measuring system according to claim 1, wherein when the amount of the change of the blood-derived light attenuation is larger than a predetermined value, the acquisition of the information by the controller is automatically started.

3. The biological signal measuring system according to claim 1, further comprising:
   a cuff which is adapted to be attachable to the subject so as to pressurize the living tissue,
   wherein the controller is configured to function as a cuff pressure controlling section which is configured to control an air pressure inside the cuff.

4. The biological signal measuring system according to claim 1, wherein
   the first light attenuation is calculated based on a ratio of the received light intensity of the first light beam at the first state when the living tissue is pressurized to the received light intensity of the first light beam at the second state, and
   the second light attenuation is calculated based on a ratio of the received light intensity of the second light beam at the first state when the living tissue is pressurized to the received light intensity of the second light beam at the second state.

5. A biological signal measuring apparatus comprising:
   a signal receiver which is configured to receive a first signal corresponding to an intensity of a first light beam that has been passed through or reflected from a living tissue of a subject, and that has a first wavelength, and a second signal corresponding to an intensity of a second light beam that has been passed through or reflected from the living tissue, and that has a second wavelength, wherein the living tissue includes neither arterial blood nor venous blood at a first state and includes at least one of arterial blood and venous blood at a second state
   a controller configured to:
   (i) acquire a first light attenuation of the first light beam based on the first signal at the first state and the first signal at the second state, and a second light attenuation of the second light beam based on the second signal at the first state and the second signal at the second state;
   (ii) acquire a blood-derived light attenuation based on the first light attenuation and the second light attenuation; and (iii) acquire information relating to a blood oxygen saturation, based on an amount of change of the blood-derived light attenuation; and an outputting device which is configured to output the identified blood oxygen saturation, wherein the controller is configured to function as a cuff pressure controlling section which is configured to control an air pressure inside a first cuff which is adapted to be attachable to the subject so as to pressurize an upstream side of the living tissue in a blood flow, wherein the controller is configured to identify a level of the blood oxygen saturation with respect to a reference value, based on an increase or decrease of the change of the blood-derived light attenuation measured during a time period between the first state and the second state.

6. The biological signal measuring apparatus according to claim 5, wherein the first light attenuation is calculated based on a ratio of the intensity of the first light beam at the first state when the living tissue is pressurized to the intensity of the first light beam at the second state, and the second light attenuation is calculated based on a ratio of the intensity of the second light beam at the first state when the living tissue is pressurized to the intensity of the second light beam at the second state.

7. A method of controlling a biological signal measuring apparatus comprising a signal receiver which is configured to receive a first signal corresponding to an intensity of a first light beam that has been passed through or reflected from a living tissue of a subject, and that has a first wavelength, and a second signal corresponding to an intensity of a second light beam that has been passed through or reflected from the living tissue, and that has a second wavelength, the method comprising:

pressurizing the living tissue of a subject such that arterial blood and venous blood are substantially removed at a first state;

releasing pressure from the living tissue such that arterial blood and venous blood return to the living tissue in a second state;

acquiring a first light attenuation of the first light beam based on the first signal received at the first state and the first signal received at the second state, and a second light attenuation of the second light beam based on the second signal received at the first state and the second signal received at the second state;

acquiring a blood-derived light attenuation based on the first light attenuation and the second light attenuation;

acquiring information relating to a blood oxygen saturation with respect to a reference value, based on increase or decrease of an amount of change of the blood-derived light attenuation; and outputting the acquired information.

8. A non-transitory computer-readable storage medium storing a program causing a computer to execute the method according to claim 7.

9. The method according to claim 7, wherein the first light attenuation is calculated based on a ratio of the intensity of the first light beam at the first state when the living tissue is pressurized to the intensity of the first light beam at the second state, and the second light attenuation is calculated based on a ratio of the intensity of the second light beam at the first state when the living tissue is pressurized to the intensity of the second light beam at the second state.

10. A biological signal measuring system comprising:

a light emitter which is configured to emit a first light beam having a first wavelength, a second light beam having a second wavelength, and a third light beam having a third wavelength;

a light receiver which is configured to output first, second, and third signals respectively in accordance with received light intensities of the first, second, and third light beams that have been passed through or reflected from a living tissue of a subject, wherein the living tissue includes neither arterial blood nor venous blood at a first state and includes at least one of arterial blood and venous blood at a second state;

a controller configured to:

(i) acquire a first light attenuation of the first light beam based on the first signal at the first state and the first signal at the second state, a second light attenuation of the second light beam based on the second signal at the first state and the second signal at the second state, and a third light attenuation of the third light beam based on the third signal at the first state and the third signal at the second state;

(ii) acquire a blood-derived first light attenuation based on a difference of two light attenuations of a first combination which is selected from the first, second and third light attenuations, and a blood-derived second light attenuation based on a difference of two light attenuations of a second combination which is selected from the first, second and third light attenuations; and (iii) identify a blood oxygen saturation based on the blood-derived first light attenuation and the blood-derived second light attenuation; and an outputting device which is configured to output the identified blood oxygen saturation, wherein the controller is configured to identify a level of the blood oxygen saturation with respect to a reference value, based on an increase or decrease of the change of the blood-derived light attenuation measured during a time period between the first state and the second state.

11. The biological signal measuring system according to claim 10, wherein the controller is configured to function as a monitoring section which is configured to periodically identify the blood oxygen saturation.

12. The biological signal measuring system according to claim 10, further comprising:

a first cuff which is adapted to be attachable to the subject so as to pressurize an upstream side of the living tissue in a blood flow, wherein the controller is configured to function as a cuff pressure controlling section which is configured to control an air pressure inside the first cuff.

13. The biological signal measuring system according to claim 11, wherein the controller functioning as the monitoring section notifies of a timing of pressurizing the living tissue, through the outputting device.

14. The biological signal measuring system according to claim 12, further comprising a second cuff which is adapted to be attached to the subject in a manner that the second cuff can pressurize the living tissue, wherein the controller functioning as the cuff pressure controlling section controls an air pressure inside the second cuff at a predetermined timing.

15. The biological signal measuring system according to claim 10, wherein the first light attenuation is calculated based on a ratio of the received light intensity of the first light beam at the first state when the living tissue is pressurized to the received light intensity of the first light beam at the second state, the second light attenuation is calculated based on a ratio of the received light intensity of the second light beam at the first state when the living tissue is pressurized to the received light intensity of the second light beam at the second state, and the third light attenuation is calculated based on a ratio of the received light intensity of the third light beam at the first state when the living tissue is pressurized to the received light intensity of the third light beam at the second state.

16. A biological signal measuring apparatus comprising:

a signal receiver which is configured to receive a first signal corresponding to an intensity of a first light beam that has been passed through or reflected from a living tissue of a subject, and that has a first wavelength, a second signal corresponding to an intensity of a second light beam that has been passed through or reflected from the living tissue, and that has a second wavelength, and a third signal corresponding to an intensity of a third light beam that has been passed through or reflected from the living tissue, and that has a third wavelength, wherein the living tissue includes neither arterial blood nor venous blood at a first state and includes at least one of arterial blood and venous blood at a second state;

a controller configured to:

(i) acquire a first light attenuation of the first light beam based on the first signal at the first state and the first signal at the second state, a second light attenuation of the second light beam based on the second signal at the first state and the second signal at the second state, and a third light attenuation of the third light beam based on the third signal at the first state and the third signal at the second state;

(ii) acquire a blood-derived first light attenuation based on a difference of two light attenuations of a first combination which is selected from the first, second and third light attenuations, and a blood-derived second light attenuation based on a difference of two light attenuations of a second combination which is selected from the first, second and third light attenuations; and (iii) identify a blood oxygen saturation based on the blood-derived first light attenuation and the blood-derived second light attenuation;

an outputting device which is configured to output the identified blood oxygen saturation, wherein the controller is configured to function as a cuff pressure controlling section which is configured to control an air pressure inside a first cuff which is adapted to be attachable to the subject so as to pressurize an upstream side of the living tissue in a blood flow, wherein the controller is configured to identify a level of the blood oxygen saturation with respect to a reference value, based on an increase or decrease of the change of the blood-derived light attenuation measured during a time period between the first state and the second state.

17. The biological signal measuring apparatus according to claim 16, wherein the first light attenuation is calculated based on a ratio of the intensity of the first light beam at the first state when the living tissue is pressurized to the intensity of the first light beam at the second state, the second light attenuation is calculated based on a ratio of the intensity of the second light beam at the first state when the living tissue is pressurized to the intensity of the second light beam at the second state, and the third light attenuation is calculated based on a ratio of the intensity of the third light beam at the first state when the living tissue is pressurized to the intensity of the third light beam at the second state.

18. A method of controlling a biological signal measuring apparatus comprising a signal receiver which receives a first signal corresponding to an intensity of a first light beam that has been passed through or reflected from a living tissue of a subject, and that has a first wavelength, a second signal corresponding to an intensity of a second light beam that has been passed through or reflected from the living tissue, and that has a second wavelength, and a third signal corresponding to an intensity of a third light beam that has been passed through or reflected from the living tissue, and that has a third wavelength, wherein the living tissue includes neither arterial blood nor venous blood at a first state and includes at least one of arterial blood and venous blood at a second state;

the method comprising:

pressurizing the living tissue of a subject;

acquiring a first light attenuation of the first light beam based on the first signal at the first state and the first signal at the second state, a second light attenuation of the second light beam based on the second signal at the first state and the second signal at the second state, and a third light attenuation of the third light beam based on the third signal at the first state and the third signal at the second state;

acquiring a blood-derived first light attenuation based on a difference of two light attenuations of a first combination which is selected from the first, second and third light attenuations at the first state when the living tissue includes neither arterial blood nor venous blood, and a blood-derived second light attenuation based on a difference of two light attenuations of a second combination which is selected from the first, second and third light attenuations at the second state when the living tissue includes at least one of arterial blood and venous blood;

identifying a blood oxygen saturation with respect to a reference value based on an increase or decrease of the change of the blood-derived first light attenuation and the blood-derived second light attenuation; and outputting the identified blood oxygen saturation.

19. A non-transitory computer-readable storage medium storing a program causing a computer to execute the method according to claim 18.

20. The method according to claim 18, wherein the first light attenuation is calculated based on a ratio of the intensity of the first light beam at the first state when the living tissue is pressurized to the intensity of the first light beam at the second state when the living tissue is not pressurized, the second light attenuation is calculated based on a ratio of the intensity of the second light beam at the first state when the living tissue is pressurized to the intensity of the second light beam at the second state, and the third light attenuation is calculated based on a ratio of the intensity of the third light beam at the first state when the living tissue is pressurized to the intensity of the third light beam at the second state.

* * * * *